United States Patent [19]

Hamilton

[11] Patent Number: 4,582,404
[45] Date of Patent: Apr. 15, 1986

[54] SAGOMETER

[76] Inventor: C. B. Hamilton, 132 Greeway Dr., Bloomingdale, Ill. 60108

[21] Appl. No.: 631,621

[22] Filed: Jul. 16, 1984

[51] Int. Cl.⁴ .............................................. A61B 3/10
[52] U.S. Cl. .................................. 351/212; 351/247
[58] Field of Search ............... 351/205, 211, 212, 214, 351/247

[56] References Cited

U.S. PATENT DOCUMENTS 2,174,308  9/1939  Hartinger ........................... 351/212
3,781,096  12/1973  Townsley ........................... 351/212

Primary Examiner—Rodney B. Bovernick
Assistant Examiner—P. M. Dzierzynski
Attorney, Agent, or Firm—Paul W. Grauer

[57] ABSTRACT

An optical instrument which measures with great accuracy certain anatomical dimensions of an eye utilizing finite light beams which strike the eye from pre-determined angles and distances. The instrument measures, among other things, the critical sagittal depth of the eye where the finite light beams converge at a recognizable point. The measurements provide optimal fitting of a contact lens to the eye.

9 Claims, 7 Drawing Figures

SAGOMETER

BACKGROUND OF THE INVENTION

This invention is in the field of optical instrumentation related to apparatus for measuring concave, planar and convex surfaces, and more particularly related to apparatus for measuring certain critical anatomical dimensions of the human eye. It is especially suited for measurements related to the sagittal depth or altitude of the corneal apex above certain points predetermined on the cornea or sclera (white) of the eye.

The portion of an eye which forms the central frontal exterior surface is called the cornea. An important application for instruments which measure the sagital characteristics of the cornea is the fitting of contact lenses. The radius of curvature must be properly analyzed in topographical terms for the proper fit of contact lenses.

The prior art instrumentation used to measure anatomical dimensions of the eye and particularly corneal curvature is principally based on the phenomena that the image size reflected from a convex surface is directly proportional to the radius of curvature of a convex object. Placido's disc exemplifies such an instrument. Placido's disc is a round, flat disc with alternating black and white rings. When light is reflected from the disc to the human cornea it gives the observer a general idea of the coreal curvature and its regularity. The larger the reflected image the greater the radius of curvature.

Since Placido's rudimentary disc, instrumentation has evolved to better plot the exterior configuration of a corneal image and then convert this form into a measurement, more or less approximating the radius of curvature. Examples of instruments of this type are the Photo-Electric Keratometer, the Keratometer and the Ophthalmometer. Such devices are disclosed in U.S. Pat. No. 3,545,846 to Wilms, U.S. Pat. No. 3,511,561 to Gambs, and U.S. Pat. No. 1,750,931 to Kellner.

The inherent disadvantage of these prior art instruments is that they measure the cornea as if it were a true spherical shape. Actually, the cornea is not spherical and may assume many different configurations. Secondly, the size of the area of the cornea measured by these prior art devices is small in comparison to the total surface area of the cornea. Third, the prior devices measure the radius of curvature of the cornea at its center where the radius of curvature is usually steeper than at the sides. The typical Keratometer or Ophthalmometer measures a central section of the cornea from about 2.5 to 3 mm in diameter, or about 5% of the total area of the cornea. The average cornea, however, is about 12 mm in diameter, and the average contact lens diameter can vary from 7 mm to 14 mm in diameter. Experience in using these prior art instruments has taught that the practitioner derives very limited information upon which to base his selection of the correct curvature for a contact lens, especially since 95% of the corneal curvature is not included in the measurement and may vary greatly from the narrow central measurement. Hence, the practitioner must rely upon his experience and trial and error to achieve a final satisfactory fit. Frequently, new lenses must be changed or re-ordered to provide a satisfactory fit for the patient. This is a costly procedure, an inconvenience for the patient and less than optimal.

The Photo-Electric Keratometer was developed to measure a larger area of the cornea. The data obtained from the instrument consists of a series of radii but similarly assumes that the cornea is configured from a series of small spherical sections. The data generated is then supplied on a computer printout to give a composite curve. The practitioner can then determine a likely curvature for the contact lenses to be fitted. Again, the selection process for the proper curvature depends upon the practitioner's experience and judgment.

The above procedures are used for fitting a "hard" contact lens; however, the proper selection of the radius of curvature of a "soft" contact lens involves even more approximation and judgment. This derives from the fact that the diameter of the "soft" contact lens is larger than the corneal diameter and, in fact, extends over the outer border of the cornea and onto the sclera (white portion of the eye around the cornea). The average radius of curvature of a cornea is approximately 7.94 mm., while the average radius of curvature of the sclera is approximately 12.25 mm. As a consequence, the practitioner must select a base curve (inside curve) for a soft contact lens of approximately 14 mm. diameter. Such a contact lens is designed to cover the entire cornea plus a small portion of the sclera. In the case of a Keratometer or Ophthalmometer, this would require a fitting based on a measurable 2 to 3 mm. section of the cornea (or 5% of the total area of the cornea) with no data whatever on the sclera; therefore, the probability of a poor fit is even greater with a "soft" lens than a "hard" lens. None of the prior art satisfactorily addresses the problem of measuring the characteristics of the sclera portion of the eye.

SUMMARY OF INVENTION

The primary object of the present invention is to measure the depth or altitude of a chord of an arc of a sagittal section of the visual anterior portion of the human eye, including the cornea and sclera, for a contact lens of any diameter. A sagittal section of the cornea can be defined as a cross-section of the cornea derived by passing a vertical or horizontal plane through the center line of vision. A chord across the arc of the cornea can then be established which equals the outside diameter of the contact lens to be fitted. Other measurements can be made with the invention, but fitting contact lenses has the highest commercial use. From the sagittal depth measurement obtained with the invention, the base curve (that is the curve on the inside of the contact lens) that is congruent with the apex of the cornea, with the edges of the lens resting more or less congruent to the corneal or scleral surface, can be determined. And this will be true whether the configuration of the cross-section of the cornea is elliptical, parabolic or some non-algebraic form.

Contact lenses are manufactured today with a spherical base curve (inside curve), primarily because present technology does not exist to economically manufacture the innumerable curvatures that would be necessary to give an exact fit for each individual and distinct eye.

The present invention will measure the sagittal depth of a singular spherical curve that will approximate the eye's multiplicity of curvatures with a single spherical curve. It will help to eliminate most contact lens failures due to poor fit.

Correct fitting of the curvature of the contact lens with the cornea and sclera, or cornea alone, will eliminate many undesirable eye reactions, such as giant papillary conjunctivitis, neo vascularization, burning, foreign body sensation, dryness, red eyes, and general discomfort.

A better physical fit of the contact lens will eliminate many follow-up visits, lens changes, lens modifications and patient dissatisfaction. The goal of fitting the proper lens during the first attempt will be easier to achieve, and will result in less trauma and safer and more comfortable contact lenses for the patient, with professional satisfaction and peace of mind for the practitioner.

The novel aspect of this invention compared to the prior art devices is that the invention measures the sagittal depth of an aspherical surface, whereas the prior art instruments measure a small arc portion of an aspherical surface and then assume that the remaining configuration of the cornea is truly spherical. In the prior art devices any error in measurement tends to be exaggerated at the outer diameters of the contact lens.

The invention comprises an optical instrument through which the practitioner observes the corneal region of the eye. The instrument houses three light sources. One light source illuminates the eye for observation by the operator. The other two (2) light sources are projected through small slits and are directed at an oblique angle to the eye thus producing slits of light upon each side of the cornea. These two slits or beams of light thus strike the eye at an angle of incidence with respect to the visual centerline of the patient. One slit of light is red and the other is green or other appropriate colors. The slits of light are projected respectively onto each side of the cornea or sclera to correspond with the outside diameter of the contact lens desired. In other words, the operator determines the outside diameter of the contact lens and then adjusts the distance between the red and green slits on the cornea to the desired diameter. The instrument is also provided with a visual fixation point for the patient such that the patient aligns his visual centerline by looking directly at the fixation point which corresponds with the optical axis of the instrument through which the eye is being observed by the operator. Thus a reference centerline is established between the eye and the instrument.

First, the two distinctively colored slits are adjusted at pre-set angles with respect to the visual centerline. Second, the slits of light are adjusted to a pre-determined distance apart on the cornea surface (the chordal distance between the slits) such that the distance equals the diameter of the lens to be selected. Next, the instrument proceeds to measure the sagittal depth of this chord, being the perpendicular distance from the chord to the apex of the cornea. The measurement of the sagittal depth is commenced by moving both slit light sources parallel to the visual center line and away from the cornea while maintaining the pre-set angles. As the slit light sources are moved away from the cornea, the red and green slits of light reflecting off the cornea surface come closer and closer together. When the slits of light converge at a single point, the apparent color changes to yellow. At this time the operator knows that he has reached the apex of the cornea. A micrometer device is incorporated in the instrument which accurately measures the distance the slit light sources are moved before they converge. By using wellknown trigonometric formulae the sagittal depth and virtual radius of curvature may be determined.

The radius of curvature is thus determined for a spherical surface which would pass through the apex of the cornea and the outside diameter of the contact lens.

Accordingly, it is an object of this invention to measure and accurately define the radius of such a curvature for the *corneal* and *scleral* regions of the human eye for fitting contact lenses.

Another object of the invention is to measure the sagittal depth of a cross-section of the corneal region of the eye.

A further object of the invention is to measure the sagittal depth of the cornea, established by three (3) anatomical points on the eye; two points being predetermined by the operator and the third point being a function of the apex of the patient's cornea.

A further object of the invention is to measure any sagittal depth in any axis perpendicular to the optical axis of the instrument.

A further object of the invention is to measure the depth of the anterior chamber of the eye.

A further object of the invention is to measure the thickness of the cornea of the eye at its apex.

Finally, it is an object of the invention to make physical measurements of the eye to assist practitioners involved in inter-ocular lens implantations.

Still other objects and advantages of the invention will be apparent from the specification below.

DESCRIPTION OF THE PREFERRED EMBODIMENT

Figure 1:
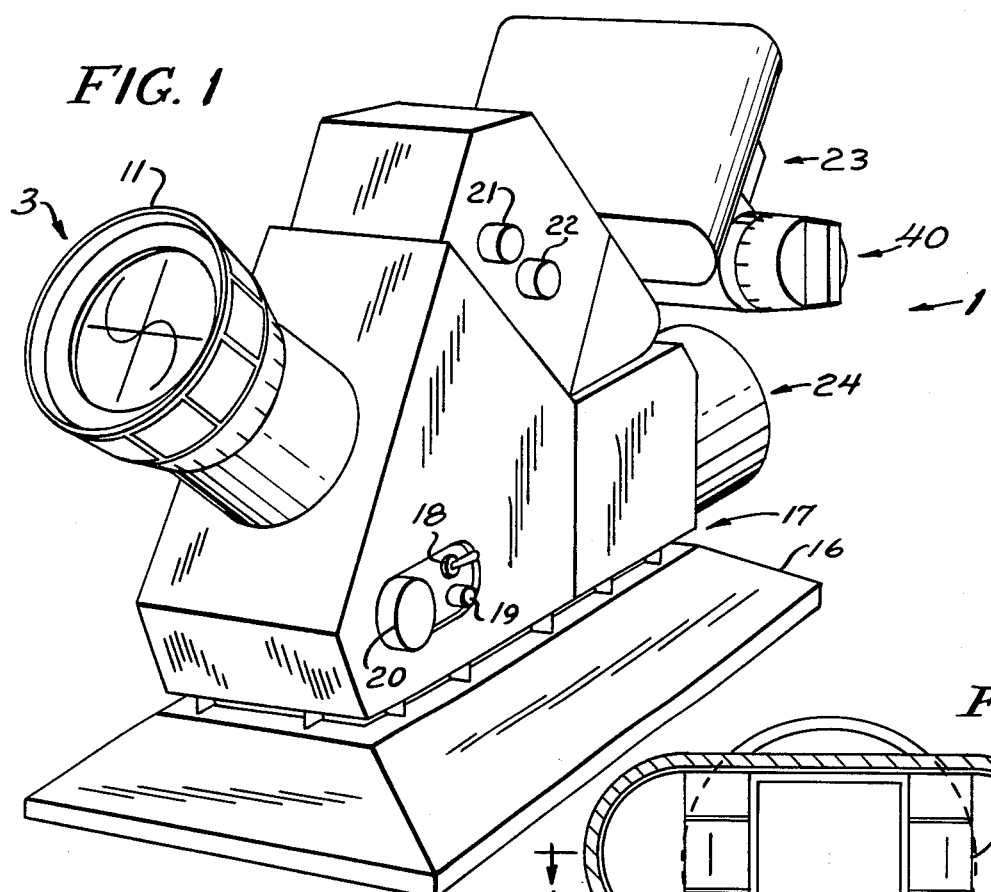
FIG. 1 is a perspective view of the sagometer.

Referring to FIG. 1, there is shown an overall perspective view of the preferred embodiment of the sagometer 1 used to measure certain anatomical dimensions. The practitioner or operator views the patient's eye 2 through the view screen assembly 3 and is provided a 2× image of the eye through the projection lens system 4 and mirror system 5 located within the housing 6 of the optical instrument.

Figure 4:
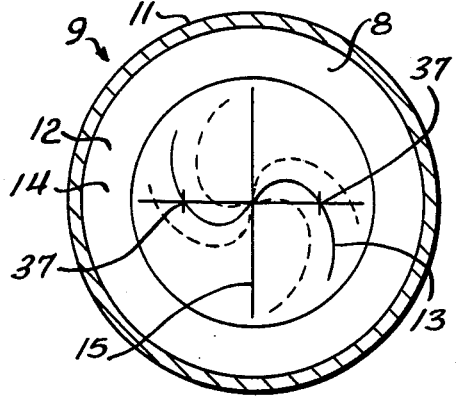
FIG. 4 is a cross-sectional view of the view screen along C—C.
Figure 5:
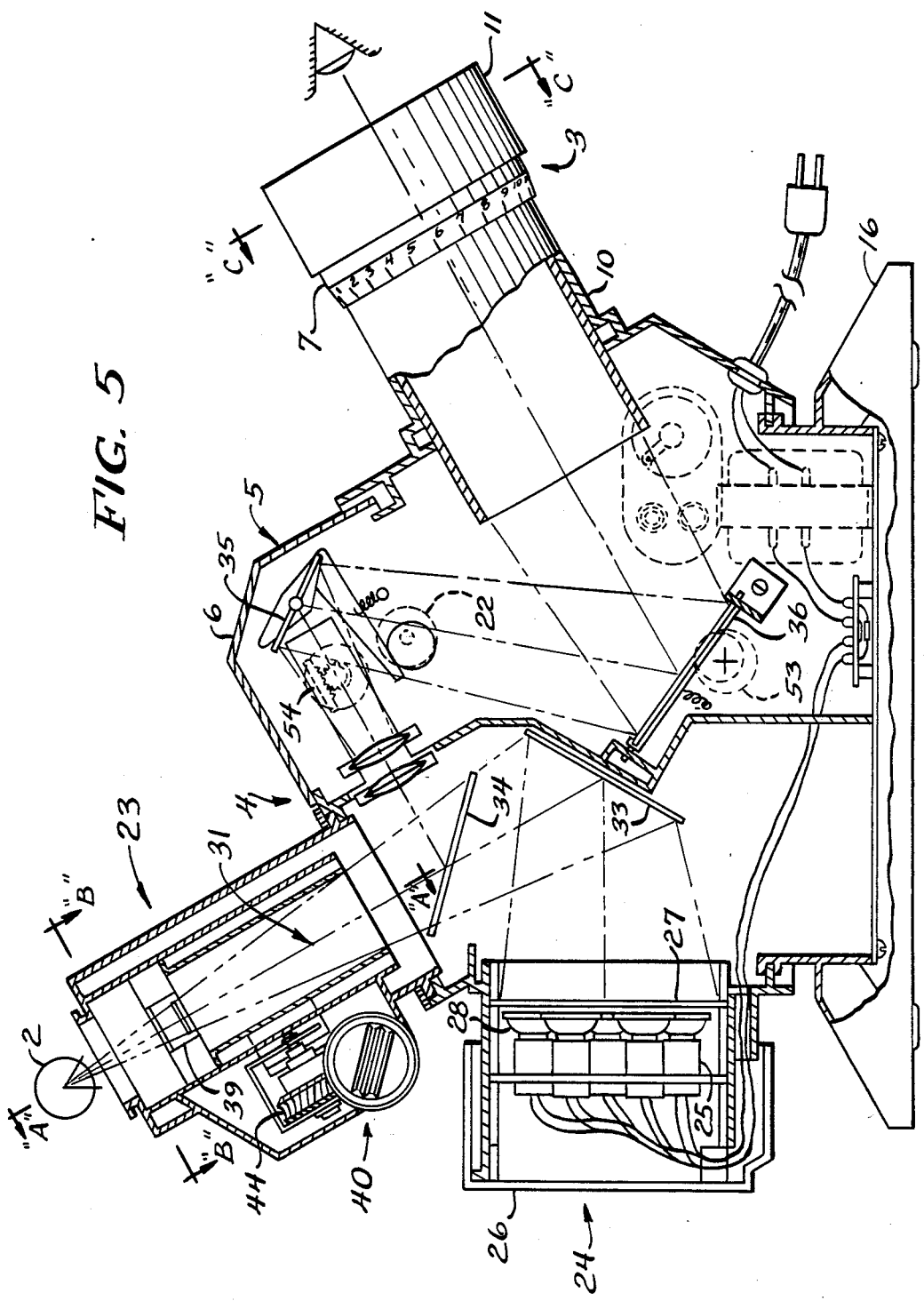
FIG. 5 is a fragmentary transverse cross-sectional view through the sagometer shown in FIG. 1.
Figure 6:
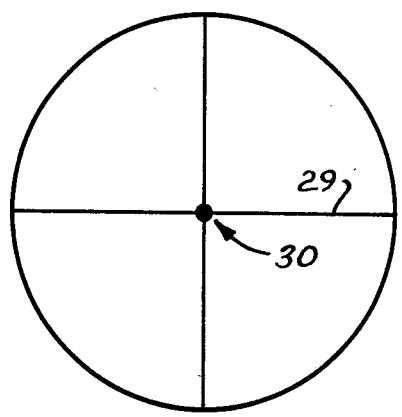
FIG. 6 is a frontal view of the diffuser.

The operator determines the contact lens diameter which will be fitted to the patient by using the indicator 7 on the view screen assembly 3. The view screen 8 through which the operator visualizes the image of the eye 2 contains the contact lens diameter selector 9 which is shown in FIG. 4. The view screen assembly 3 is mounted to the housing 6 of the instrument by a fixed barrel 10. At the end of the fixed barrel 10, distal to the housing 6 there is attached a collar 11 which rotates about the axis of the barrel which is coincident with the optical axis of the view screen assembly 3. The collar 11, which can be manually rotated by the operator is attached to a clear mylar screen 12. Superimposed upon this clear mylar screen 12 is a spiroidal curve 13 as shown in FIG. 4. Adjacent to the collar 11 is a contact lens diameter indicator 7 which is graduated in millimeters. The indicator 7 is congruent to the fixed barrel 10 and the collar 11 as shown in FIG. 5.

Another mylar screen 14 has a matte finish with superimposed cross-hairs 15 and is positioned directly underneath the clear spiroidal screen 12. These cross-hairs 15 serve as a reference for positioning the 2× image of the eye 2 upon the view screen 3. As viewed by the operator, shown in FIG. 4, the cross-hairs 15 of the cross-hair screen 14 appear to intersect with the spiroidal curves 13.

FIG. 1 shows that the instrument housing 6 is supported by a base 16 with ventilation ports 17 located between the housing 6 and the base 16. A master switch 18, fuse receptacle 19, and rheostat control 20, all known in the art, are grouped together near the base 16 on the right side of the instrument (with respect to the operator) as shown in FIG. 1. The focus 21 and vertical image 22 control knobs are also shown in FIG. 1 located near the top of the instrument on the right side.

Figure 3:
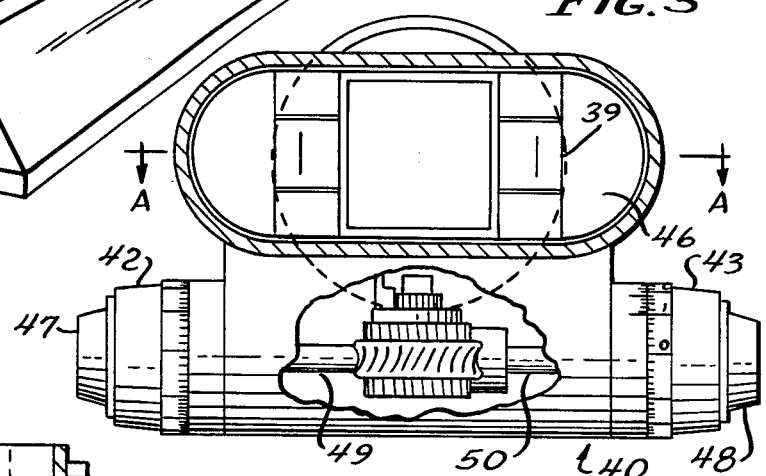
FIG. 3 is a cross-sectional view along B—B of the ocular portion of the sagometer, together with a cut-away view of the worm gear set.
Figure 2:
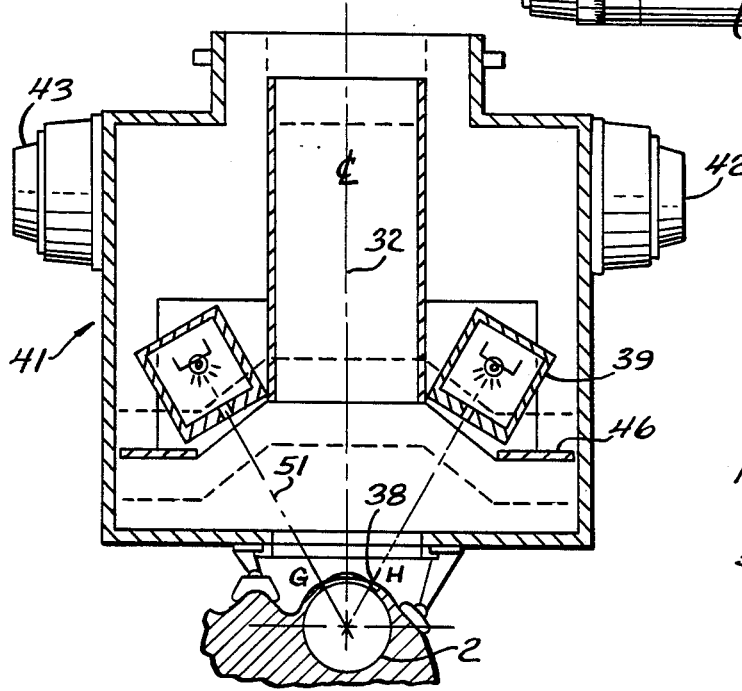
FIG. 2 is a fragmentary cross-sectional view along A—A of the ocular portion of the sagometer.

Opposite the operator's viewing screen assembly 3 is located the portion of the instrument where the patient places his eye 2, referred to as the ocular assembly 23, and is shown in detail in FIGS. 2 and 3. FIG. 2 shows how the plurality of movable slit light beams are directed upon the eye while FIG. 3 illustrates a means for moving the slit light beams through use of the micrometer assembly. A pair of distinctively colored slit light beams is provided, however, red and green are the preferred colors. The illuminator 24 which provides light to illuminate the eye 2 for the operator is located beneath the ocular assembly 23 as shown in FIG. 5.

Figure 7:
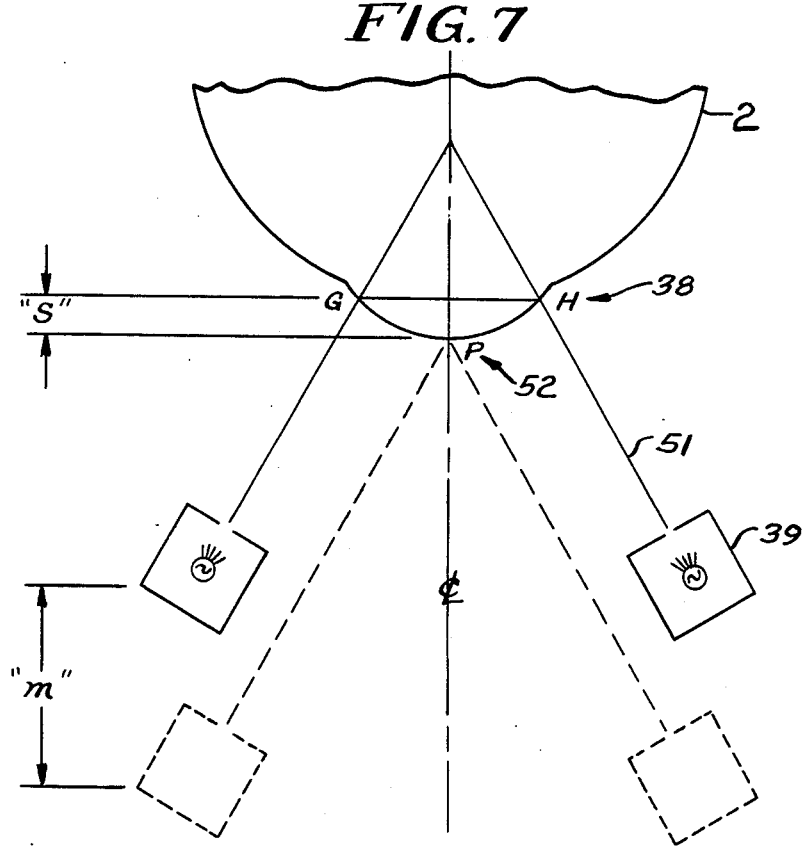
FIG. 7 is a schematic diagram of the relationship between the slit light beams and the eye.

Referring now to FIG. 5, there is shown the internal portions of the preferred embodiment for the present invention. There is shown the means for reflecting and illuminating the image of the eye 2 upon the view screen 3 together with the details of the illuminator 24. The illuminator 24 consists of a light source 25 contained within a cover 26 attached to the housing 6. A rheostat control 20 is provided to vary the light intensity as desired by the practitioner. The light from the illuminator 24 is first diffused by a diffuser 27. The diffuser 27 is located directly in front of the illuminator light source 25. A preferred light source for the illuminator 24 comprises multiple mini-reflector lamps 28. The diffuser 27 contains a cross-hair for reference 29 and a red dot 30 or other marking to act as a fixation point for the patient as shown in FIG. 7. In other words, the patient looks or "fixes" upon the red dot 30 during the examination.

Referring to FIG. 5, it can be seen that if the patient fixes his vision upon the dot 30, his line of vision 31 will then be co-incident with the optical center line or axis 32 of the ocular assembly 23 and similarly with the rest of the instrument. After the illuminator light passes through the diffuser 27, it is then reflected off the illuminator mirror 33 and on to the patient's eye 2 as shown in FIG. 5 and is then reflected back to a 50% mirror (50% reflective and 50% transparent) 34 and ultimately to the practitioner through the projection lens system 4, a vertical adjustment mirror 35, a horizontal adjustment mirror 36, and the view screen 3.

The so-called 50% mirror 34 in FIG. 5 is a combination semi-transparent and semi-reflective mirror. In the preferred embodiment, 50% transparent and 50% reflective is the percentage of choice.

The ocular assembly 23 shown in cross-section in FIG. 5 is the portion of the sagometer 1 which the patient looks into and contains the slit lamp casings 39 and the micrometer assembly 40 to move the casings 39.

The view screen assembly 3 houses two mylar screens, one with a cross-hair and one with a spiroidal curve superimposed upon the screen, which are shown superimposed upon one another in FIG. 4. The cross-hair screen 14 remains fixed while the screen 12 with the spiroidal curve 13 is allowed to rotate. The contact lens diameter selector 9 is designed to allow the operator to establish and superimpose the diameter of the selected contact lens directly upon the 2× image of the eye while the practitioner observes the eye 2 through the view screen assembly 3. This is accomplished by rotating the lens diameter selector collar 11 to the preselected lens diameter shown on the indicator 7. The indicator 7 is graduated in millimeters, and the intersection 37 of the spiroidal curve 13 with the cross-hairs 15 shown in FIG. 4 will indicate to the operator the desired diameter of the contact lens.

The operator is then in a position to adjust the slit lamp cursors 38, shown in FIGS. 2 and 3, to establish points "G" and "H" shown in FIG. 7. It has been determined that an angle of 30° is the preferred angle between the slit light beams and the optical axis of the view screen assembly, however, other pre-determined angles are workable. Once the operator has adjusted the slit lamp cursors 38 so that finite beams of light project through points "G" and "H" respectively and intersect on the center line, the operator is then prepared to take the required measurements.

The micrometer assembly 40 is shown in FIG. 3. It simply provides a means to measure the parallel movement of the movable slit light sources 41. The micrometer assembly 40 has two dials on either side of the ocular assembly 23. The left dial 42 is graduated from zero to twenty millimeters and is the coarse adjust dial. The right dial 43 is graduated from zero to one millimeter and is the fine adjust dial. The fine adjust dial can be disengaged from its worm gear 44 by operating the platen lever 47 adjacent to the coarse adjust dial. With the fine adjust dial 43 disengaged, the operator can turn the coarse adjust dial 42 in either direction, which will cause the frame 46 within the ocular assembly 23 to move toward or away from the patient's eye 2. With the fine adjust dial 43 engaged, the operator can turn the fine adjust dial 43 counter clockwise which will cause the frame 46 within the ocular 23 to move away from the patient's eye 2 and also cause the coarse adjust dial 42 to register one millimeter for every full rotation of the fine adjust dial 43.

Both the coarse and fine adjust dials are equipped with platen levers 47, 48 which release the dials from their shafts 49, 50 and allow the operator to set the dial scales at zero without moving the frame 46 within the ocular 23. The micrometer 40 is then used to measure the distance that the slit lamp beams 51 must traverse before they converge at the apex of the cornea 52 represented by point P in FIG. 7. The distance that the slit lamp casings 39 must be moved is represented by "m" as shown in FIG. 7. When distance "m" has been established from the micrometer, well-known trigonometric formulae can be used to determine the sagittal depth "S" which is then utilized in determining the radius of curvature for the chord represented by line GH.

A projection lens system 4 is shown in FIG. 5. This lens system 4 is known in the art and conventional focus controls are provided in the housing 1 of the optical instrument. The optical axis of the lens system 4 is appropriately aligned with the 50% mirrors 34 to magnify and focus the image of the eye 2. Conventional controls both focus the corneal region of the eye for the practitioner and magnify it appropriately for ease of observation and accurate measurement. The magnification of choice is 2×. Horizontal 53 and vertical 22 image controls, known in the art, are provided to adjust the image of the patient's eye 2 upon the view screen 3.

The amount of general illumination to the patient's eye 2 can be controlled by the rheostat 20 on the right side of the instrument, as seen by the operator.

Means are provided for centering the image of the eye 2 with respect to the view screen 3. The preferred embodiment comprises two dials for this purpose. The first, marked "Vert." 22 is on the operator's right side above the rheostat dial 20, and by turning in either direction allows the operator to align the image by way of the reflected diffuser image on the patient's eye with the horizontal hair line 37 on the view screen 3. The second dial 53, marked "Horiz." is on the operator's left near the bottom of the housing 6. It is depicted by the hidden lines in FIG. 5 just below the horizontal adjustment mirror 36. Similarly, by turning the "Vert." dial 22 in either direction, it allows the operator to align the diffuser image of the eye with the vertical hair line on the view screen 3.

The magnification 54 and focus 21 controls are two dials on the left side and right side respectively of the sagometer 1, magnification 54 marked "Mag." on the operator's left, and focus 22 marked "Foc." on the right. Both controls allow the operator to calibrate the image in the view screen to true 2× focused magnification.

In the preferred embodiment, the slit lamp beams 51 would comprise two distinctively colored beams of light, one red and one green which, when they converge, form a yellow light at point P 52.

While not shown in the preferred embodiment, there are means, both mechanical and electrical, well-known in the art, which would convert the parallel movement measurement, dimension "m", to the radius of curvature for the given chord GH. Thus, the operator could read the radius of curvature directly from the instrument. Such means could be readily adapted to the preferred embodiment or other embodiment to provide such direct readings.

Again, referring to FIG. 2, it is seen that a plurality of light sources 41 of any visible range in the electromagnetic spectrum, colored or polarized, could be utilized for the slit lamp cursors 38. However, the preferred embodiment utilizes two (2) slit lamp cursors 38 of colored light since this has been found adequate for the purposes of this instrument.

It can also be seen in FIG. 5 that the projection lens system 4 is located above the semi-transparent mirror 34, and this is simply a matter of choice of design.

Additionally, in FIG. 2, it is seen that a plurality of rational geometric curves such as sinoidal, paraboloidal, etc., could be used for the contact lens' diameter selector 9 in lieu of the chosen spiroidal curves 13. This, once more, is no more than choice of design.

While a preferred embodiment has been described, it is understood that the invention is not restricted to this particular preferred embodiment and many alternatives and mechanical variations would be possible without affecting the novel aspects of the invention.

I claim:

1. An optical instrument for measuring certain anatomical dimensions of the eye, comprising:
   a housing;
   a view screen assembly, with an optical axis, mounted to the housing;
   an ocular assembly, with an optical axis, mounted to the housing;
   an illuminator adapted to the housing;
   an illuminator mirror positioned within the housing to reflect light from the illuminator to the eye;
   a fixation point mounted to the illuminator upon which the eye can focus thereby aligning the optical axis of the ocular assembly with the line of vision of the eye;
   a semi-transparent mirror positioned in the housing to receive the image of the illuminated eye;
   a lens system, with an optical axis, mounted within the housing to magnify and focus the eye upon the view screen assembly;
   means for centering the image of the eye with respect to the optical axis of the view screen assembly;
   means for reflecting and illuminating the image of the eye to be examined upon the view screen assembly;
   a plurality of movable slit light sources within the ocular assembly adapted to project finite light beams upon the eye with respect to the optical axis of the ocular assembly;
   means to move the plurality of movable slit light sources along an axis parallel to the optical axis of the ocular assembly until the slit light beams converge at a common point; and
   means to measure the parallel movement of the movable slit light sources.

2. The optical instrument of claim 1 wherein the plurality of movable slit light sources comprise:
   a pair of distinctively colored slit light beams.

3. The optical instrument of claim 1 wherein the view screen assembly comprises:
   a fixed barrel;
   a collar rotatably mounted to the fixed barrel at its distal end;
   a contact lens diameter indicator attached to the collar;
   a spiroidal screen rotatably mounted to the fixed barrel in such a way that the screen rotates about the optical axis of the view screen assembly and is connected to the collar; and
   a cross-hair screen mounted to the fixed barrel in such a way that the cross-hair screen is co-planar with and adjacent to the spiroidal screen.

4. The optical instrument of claim 1 wherein the means for reflecting and illuminating the image of the eye to be examined upon the view screen comprises:
   a combination semi-transparent and semi-reflective mirror.

5. The optical instrument of claim 1 wherein the plurality of movable slit light sources comprises:
   a lamp for each light source;
   a lamp casing with a slit; and
   means for connecting the lamp casing to the means which measures the parallel movement of the slit light sources.

6. The optical instrument of claim 1 wherein the means to measure the parallel movement of the movable slit light sources comprises:
   a micrometer assembly.

7. The optical instrument of claim 1 further comprising:
   means to convert the parallel movement measurement of the slit light sources directly to the radius of curvature measurement.

8. The optical instrument of claim 1 further comprising:
   a diffuser mounted to the illuminator to diffuse the light from the illuminator.

9. The optical instrument of claim 1 wherein the plurality of movable slit light sources comprise:
   a pair of beams, one (1) red and one (1) green colored.

* * * * *